United States Patent [19]
Nelis

[11] Patent Number: 5,861,270
[45] Date of Patent: Jan. 19, 1999

[54] **ENZYMATIC METHOD FOR DETECTING COLIFORM BACTERIA OR *E. COLI***

[75] Inventor: Jozef Constantia Frans Hans Nelis, Horebeke, Belgium

[73] Assignees: Universiteit Gent, Gent; Studie- en Samenwerkingsverband Vlaams Water, Antwerpen, both of Belgium

[21] Appl. No.: 836,140
[22] PCT Filed: Nov. 7, 1995
[86] PCT No.: PCT/BE95/00102
§ 371 Date: Jul. 14, 1997
§ 102(e) Date: Jul. 14, 1997
[87] PCT Pub. No.: WO96/14431
PCT Pub. Date: May 17, 1996

[30] Foreign Application Priority Data

Nov. 7, 1994 [WO] WIPO ............ PCT/BE94/00083

[51] Int. Cl.[6] ............... C12Q 1/04; C12Q 1/10; C12Q 1/54; G01N 33/53
[52] U.S. Cl. ............... 435/34; 435/38; 435/14; 435/848; 435/849; 435/968
[58] Field of Search ............... 435/34, 38, 14, 435/848, 849, 968

[56] References Cited

FOREIGN PATENT DOCUMENTS 9614431  5/1996  WIPO .

OTHER PUBLICATIONS

Nelis et al; Proceedings of the Water Quality Tech. Conference AWWA; pp. 1663–1673; Nov. 1993.

De Marie et al; J. of Clinical Microbiology; pp. 255–258, Aug. 1984.

*Primary Examiner*—Louise N. Leary
*Attorney, Agent, or Firm*—Dorsey & Whitney LLP

[57] ABSTRACT

A two stage enzymatic method for the detection of coliform bacteria or *E. coli* wherein bacteria are concentrated on a membrane filter. This filter is placed on a growth medium containing nutrients, including preferably minerals, a protein hydrolysate and a sugar, preferably maltose or a polyalcohol, preferably mannitol, an inducer of a marker enzyme, in particular β-galactosidase or β-glucuronidase and inhibitors of the growth of competing bacteria. After a preincubation step, the filter is placed on an assay medium containing a fluorogenic or chemiluminogenic enzyme substrate and a membrane permeabilizer. The membrane filter and the assay medium are incubated to allow cleavage of the enzyme substrate producing fluorescent or chemiluminescent microcolonies on the membrane filter after triggering of light emission.

36 Claims, 9 Drawing Sheets

ENZYMATIC METHOD FOR DETECTING COLIFORM BACTERIA OR *E. COLI*

RELATED APPLICATIONS

This application claims the priority of PCT Application No. PCT/BE95/00102/, filed Nov. 7, 1995, and PCT Application No. PCT/BE94/00083, filed Nov. 7, 1994, which are incorporated herein by reference.

The present invention relates to an enzymatic method for detecting coliform bacteria, in particular total coliform bacteria faecal coliform bacteria or *E. coli*, in a liquid or liquefied sample, for example drinking or recreational water, comprising the steps of:

a) concentrating the bacteria on a membrane filter;

b) placing the membrane filter and the bacteria concentrated thereon on a growth medium containing nutrients to support propagation of the bacteria and an inducer for inducing a marker enzyme in the course of their growth and metabolism;

c) preincubating the membrane filter and the bacteria concentrated thereon to form microcolonies of these bacteria on the membrane filter and to produce said marker enzyme; and d) making the microcolonies visible by means of luminescence.

Coliform bacteria are indicators of the sanitary quality of water and food. Total coliforms (TC) in water originate from soil or organic vegetal material. Faecal (thermotolerant) coliforms (FC) and *E. coli* in particular inhabit the intestine of humans and animals and are indicators of faecal pollution.

Traditional processes for detecting coliforms and *E. coli* by membrane filtration are based on lactose fermentation in conjunction with confirmatory tests and require 48 to 96 hours to complete. A procedure is conventionally considered to be rapid if it takes 24 hours or less to perform. However, a 24 hours method is still not rapid enough to be used for the analysis of drinking water in emergency situations, e.g. after breakdowns in the water supply or construction works to the distribution system. In those cases, the detection of at least 1 coliform bacterium per 100 ml of water should be feasible within the ordinary work shift of 8 hours and preferably in maximum 7 hours to demonstrate the potability of the water and, hence to avoid unnecessary warnings to the public about the contrary.

Existing rapid (24 hours) membrane filtration methods for the detection of coliform bacteria, in particular TC and *E. coli* rely on the demonstration of the activity of 2 specific marker enzymes in the bacterial colonies, i.e. β-galactosidase and β-glucuronidase, respectively, which the bacteria produce as they grow and metabolize. The presence of these enzymes is revealed by the ability of the bacteria present on the membrane filter to cleave chromogenic substrates added to the growth medium such as 5-bromo-4-chloro-3-indolyl-β-D-galactopyranoside (X-gal) for β-galactosidase and 5bromo-4-chloro-3-indolyl-β-D-glucuronide (X-gluc) for β-glucuronidase. The chromogenic substrates themselves are not colored so that the detection of colored colonies on the membrane filter indicates the presence of the enzyme and, hence, of the bacteria. See e.g. Manafi and Kneifel, Zentralbl. Hyg. 189:225–234 (1989), Brenner et al., Appl. Environ. Microbiol. 59:3534–3544 (1993) and Frampton and Restaino, J. Appl. Bacteriol. 74:223–233 (1993).

Similarly, fluorogenic substrates, e.g. 4-methylumbelliferyl-β-D-galactopyranoside (MU-gal) or 4-methylumbelliferyl-β-D-glucuronide (MUG) added to the growth medium can be cleaved by bacterial β-galactosidase and β-glucuronidase, respectively, to yield a fluorescent product, 4-methylumbelliferone (4-MU). The fluorogenic substrates themselves do not fluoresce so that the detection of fluorescent colonies on the membrane filter indicates the presence of the enzyme and, hence, of the bacteria. Currently, the most rapid fluorescent method to detect TC on a membrane filter using MU-gal as a substrate for β-galactosidase takes 16–24 hours to complete (Brenner, cited above). For *E.coli* the minimal detection time obtained by using MUG as a substrate for β-glucuronidase is 7.5 hours (Sarhan and Foster, J. Appl. Bacterial. 70:394–400 1991)). The Berg et al. U.S. patent and scientific publication disclose a method to detect faecal (thermotolerant) coliforms on a membrane filter using an agar growth medium containing MU-gal as a substrate for β-galactosidase and an incubation temperature of 41.5° C., in a time period of 6 hours (Berg et al., U.S. Pat. No. 5,292,644 and Appl. Environ. Microbiol. 54:2118–2122 (1988)). However, the time to detect total coliforms which grow at 35°–37° C. and possess lower β-galactosidase activity than the thermotolerant coliforms exceeds 8 hours. *E. coli* cannot be detected specifically using this method.

SUMMARY OF THE INVENTION

The object of the present invention is therefore to provide a membrane filtration method which allows to detect coliform bacteria, in particular FC but especially also TC and *E. coli* in a liquid or liquefied sample in a shorter time, for TC for example within a detection time of 7 hours.

To this end, themethod according to the present invention is characterized in that said microcolonies are made visible by an enzyme assay comprising:

removing the membrane filter from the growth medium after said preincubation step (c);

treating the microcolonies on the membrane filter with a membrane permeabilizer and contacting them with a chemiluminogenic or fluorogenic substrate for said marker enzyme;

incubating the microcolonies to allow cleavage of said substrate so as to produce a chemiluminescent or fluorescent product; and triggering light emission from the chemiluminescent or fluorescent product produced by the microcolonies.

The use of a two-stage approach in which the enzyme assay step is separated from a so-called preincubation step meant to propagate the bacteria and to induce the marker enzyme, allows to add a membrane permeabilizer and to avoid competition for the enzyme between the substrate and the inducer. The rationale for including a membrane permeabilizer in the assay is to promote the rapid uptake of the substrate by the bacteria. Use is made in particular of membrane permeabilizers that disrupt both the outer and the cytoplasmic membrane of coliforms and *E. coli*, for example polymyxin B or colistin, or a mixture of one of these with lysozyme. In the known one-stage methods, for example the method disclosed by Berg et al. in U.S. Pat. No. 5,292,644, such membrane permeabilizers can not be used since they are bactericidal and can thus not be added to the growth medium.

A two-stage method has already been disclosed by the present inventor, i.e. by Nelis et al. in Proceedings of the Water Quality Technology Conference, (AWWA), Miami, Fla, 7–11 Nov., 1993, pp. 1663–1673 In this known method, the bacteria concentrated on the filter are however transferred into a liquid growth medium, the filter itself being removed so that no microcolonies are formed in the medium. Instead, a homogeneous mixture of bacteria is obtained from which the overall light emission is measured by means of a luminometer or a fluorometer. It was found now, however, that in such liquid detection technique non-coliform bacteria which contain β-galactosidase or β-glucuronidase may often interfere. Although the growth of such non-coliform bacteria can be inhibited, the amount of marker enzyme present in these non-coliform bacteria influences the measurement when large numbers of them are present in the sample. In the method according to the present invention, such an interference is excluded since the non-coliform bacteria can be prevented from forming microcolonies, even if they are present in a much larger number than the coliform bacteria.

In a particular embodiment of the present invention, use is made of a membrane filter which is more hydrophobic than generally used cellulose ester filters, use being in particular made of a membrane filter made of polyvinylidenedifluoride (PVDF).

It was found that the use of such hydrophobic membrane filters results in intensified light emission by the bacterial microcolonies.

In a preferred embodiment of the present invention, said inducer is selected from the group comprising isopropyl-β-D-thiogalactopyranoside for β-galactosidase and isopropyl-β-D-thioglucuronide and pnitrophenyl-β-D-alucuronide for β-glucuronidase.

These inducers were found to be more efficient than the inducers used in traditional media.

In a further preferred embodiment of the present invention, use is made as said growth medium of a medium containing mineral nutrients, a protein hydrolysate, in particular tryptone, and a sugar, preferably maltose, or a polyalcohol, preferably mannitol.

The use of such a growth medium in the preincubation step combines the properties of efficient growth promotion, good recovery of stressed coliforms/$E.$ $coli$ on one hand with a low luminescent background and minimal effects of quenching of light emission on the other hand.

In a still further preferred embodiment of the present invention, use is made of fluorogenic substrates different from the above mentioned MU-gal and MUG, in particular of 4-trifluoromethylumbelliferyl-β-D-galactopyranoside (TFMU-gal) or 4-trifluoromethylumbelliferyl-β-D-glucuronide (TFMUG), but preference is given to chemiluminogenic substrates. The latter have not been applied so far for the detection of bacterial colonies grown on a membrane filter but yield more sensitivity than the presently used substrates.

The present invention also relates to a growth medium for use in the method according to the invention, which medium is characterized in that it contains mineral nutrients, a protein hydrolysate, in particular tryptone, an inducer for inducing a marker enzyme in the course of growth and metabolism of coliform bacteria, in particular β-galactosidase or β-glucuronidase, and a sugar, preferably maltose or a polyalcohol, preferably mannitol.

Before giving a more detailed description of the invention, the meanings of some specific terms used in this description are first of all given hereinafter:

The term total coliforms (TC) refers to bacteria belonging to either of four genera, i.e. Escherichia, Enterobacter, Klebsiella or Citrobacter, and possessing the enzyme β-galactosidase.

The term faecal coliforms (FC) refers to (thermotolerant) bacteria belonging to the group of the coliforms and inhabiting the intestine of humans and animals. These faecal coliforms are indicators of faecal pollution and posses also the enzyme β-galactosidase, the particular species $E.$ $coli$ possessing further the enzyme β-glucuronidase. Detection of the faecal coliforms can be done by incubating them at a higher temperature (41.5°–44° C.) than the temperature used for detecting total coliforms (about 35°–37° C.).

The term preincubation refers to a step in the method of this invention in which a membrane covered with one or more bacteria, the latter originating from a filtered sample, is placed on a growth medium and kept at a certain temperature for a given time in order to propagate the bacteria and to induce the marker enzyme.

The term membrane permeabilizer refers to any compound capable of disrupting both the outer and the cytoplasmic membrane of bacteria so as to facilitate the uptake of chemicals.

The term enzyme assay refers to a step distinct from the growth step in the method of this invention in which a substrate is cleaved by a marker enzyme, in particular β-galactosidase or β-glucuronidase, present in the bacteria, the cleavage product then being determined by virtue of the light it emits after photochemical or chemical excitation.

The term luminescence refers to fluorescence or chemiluminescence.

The term fluorescence refers to a physicochemical process in which a molecule emits light of a certain wavelength after photochemical excitation, i.e. with light of a shorter wavelength.

The term chemiluminescence refers to a physicochemical process in which a molecule emits light after chemical excitation with a formulation termed "accelerator".

The term fluorogenic substrate refers to a compound which itself is non-fluorescent but which contains a structural part, i.e. the so-called fluorescent product, that does emit light when liberated from the parent compound and photochemically excited.

The term chemiluminogenic substrate refers to a compound which itself is not chemiluminescent but which contains a structural part, i.e. the chemiluminescent product, that does emit light when liberated from the parent compound and chemically excited.

The sample to be analyzed is liquid or liquefied and is suspected of containing at least 1 TC, 1 FC or 1 $E.$ $coli$/100 ml. Typical samples to which the method of the invention can be applied include drinking water, bathing water or liquid extracts of foods or pharmaceuticals.

The first step of a particular embodiment of the method according to this invention consists of concentrating the bacteria present in for example a 100 ml liquid or liquefied sample on a filter, more particularly on a bacterial membrane filter with a pore size of 0.22 $\mu$m–0.45 $\mu$m and a diameter of for example 47 mm. The membrane filter is preferably made of polyvinylidene difluoride (PVDF) (Durapore®, obtainable from Millipore, Bedford, Mass.) because this material has been found to enhance the final fluorescence or chemiluminescence of the bacterial microcolonies. Other useful materials include polytetrafluoroethylene, polycarbonate, nylon or cellulose esters, particularly cellulose nitrate.

The second step is placing the membrane filter containing the bacteria on a solid, semi-solid or liquid growth medium in a 55 mm petri dish containing agar or an absorbent cellulose pad as an inert matrix. This medium includes in particular a protein hydrolysate, preferably tryptone (for example 0.5%), yeast extract (for example 0.3%), monoammonium phosphate (for example 0.2%), magnesium sulfate (for example 0.005%), dipotassium hydrogen phosphate (for example 0.1%) and a sugar, preferably maltose (for example 0.5%) or a polyalcohol, preferably mannitol (for example 0.5%). This medium is called hereinafter the Improved Luminescence Medium (ILM). A further improved medium can however be obtained by the omission of yeast-extract from the ILM resulting in more intensely luminescent colonies on the membrane filter. The ILM growth medium further contains sodium dodecyl sulfate (for example 0.01%), bile salts (for example 0.01%) and the antibiotic cefsulodin (for example 0.001%) as inhibitors of competing non-target bacteria. It further contains a compound to induce one of the said marker enzymes, that is for example isopropyl-β-D-thiogalactopyranoside (for example 0.001%) or melibiose (for example 0.01%) an inducer of β-galactosidase and p-nitrophenyl-β-D-glucuronide (for example 0.05%), isopropyl-β-D-thioglucuronide (for example 0.001%), o-nitrophenyl-β-D-glucuronide (for example 0.05%) or methyl-β-D-glucuronide (for example 0.005%) to induce β-glucuronidase. The ILM used in the method according to this invention, and especially the ILM without yeast extract, yields considerably more intense fluorescent and chemiluminescent microcolonies after a given time than a variety of other selective media for TC and E. coli, including m Endo agar LES, MacConkey agar, m TEC agar, m FC agar, EC agar, Lauryl Tryptose agar, Tryptone Bile agar, m T7 agar, Lauryl Sulphate agar, the MUG-7 medium as described by Sarhan and Foster (cited above) and the medium disclosed in the Berg et al. U.S. patent (cited above).

The third step is the so-called preincubation and consists of incubating the membrane filter and the growth medium at a suitable temperature (for example 35°–370° C. for total coliforms or 41.5°–44° C. for faecal coliforms and especially for E. coli), preferably in a water bath, for a suitable time, to allow the bacteria to multiply and to produce sufficient marker enzyme detectable by fluorescence or chemiluminescence.The required preincubation time is usually comprised between 4 and 6.5 hours depending on whether a fluorogenic or a chemiluminogenic substrate is used.

The fourth step consists of removing the membrane filter from the growth medium and placing it on an absorbent cellullose pad impregnated with a medium to assay the marker enzyme. This assay medium contains in particular a fluorogenic substrate for either of the two marker enzymes, that is preferably TFMU-gal ($\lambda$exc 394, $\lambda$em 489 nm) (β-galactosidase) or TFMUG ($\lambda$exc 394, $\lambda$em 489 nm) (β-glucuronidase). The common fluorogenic substrates MU-Gal (β-galactosidase) or MUG (β-glucuronidase) can also be used but yield a lower sensitivity. A disandvantage of the latter two compounds is that they require spraying of the membrane filter with sodium hydroxide to yield optimal fluorescence. Other analogues of MU-gal that could also be considered as substrates for β-galactosidase, including 3-acetyl-7-(β-D-galactopyranosyloxy)coumarin ($\lambda$exc 420, $\lambda$em 459 nm), 3-(2-benzoxazolyl)-7-(β-D-galactopyranosyloxy)coumarin and 1-(β-D-galactopyranosyloxy)-pyrene-3,6,8-tris-(dimethylsulfonamide) ($\lambda$exc. 495 nm, $\lambda$em. 550 nm at pH 9) (see Koller et al., Appl. Fluoresc. Technol. 1,15–16 (1989)) are in principle more sensitive and specific than MU-gal itself as their wavelengths of excitation and emission have shifted to higher values and/or because they have increased molar absorption coefficients. Non-umbelliferyl fluorogenic galactopyranosides and glucuronides can in principle also be used, for example fluorescein di-β-D-galactopyranoside or fluorescein-di-β-D-glucuronide and derivatives thereof such as $C_{12}$-fluorescein-di-β-D-galactopyranoside or $C_{12}$-fluorescein-di-β-D-glucuronide (ImaGene Green, Molecular Probes, Eugene, OR) or resorufin-β-D-galactopyranoside or resorufin-β-D-glucuronide (ImaGene Red, Molecular Probes). A still higher intrinsic sensitivity is associated with the chemiluminogenic AMPGD (3-(4-methoxyspiro[(1,2-dioxetane-3,2'-tricyclo[3.3. 1.1$^{3.7}$]decan]-4-yl)phenyl)-β-D-galactopyranoside) or derivatives thereof, in particular chloro derivatives (for example Galacton® (a mono-chloro derivative of AMPGD), Galacton-Plus® (a di-chloro derivative of AMPGD) (β-galactosidase) available from Tropix, Inc., Bedford, Mass.) and Glucuron® (3-(4-methoxyspiro [1,2-dioxetane-3,2'-(5'-chloro)-tricyclo[3.3.1.1$^{3.7}$]decan]4-yl)phenyl)-β-D-glucuronide) or derivatives thereof (β-glucuronidase) (Tropix Inc.), chemiluminescence in general being superior in sensitivity to fluorescence by the order of magnitude. AMPGD and Glucuron have been used as substrates in gene reporter assays. See e.g. Jain et al., Anal. Biochem. 199:119–124 (1991) and Bronstein et al., Anal. Biochem. 219:169–181 (1994). Furthermore, the assay medium will contain a membrane permeabilizer, preferably polymyxin B sulfate or colistin methanesulfonate, or a mixture of one of these with lysozyme, and buffering substances to adjust z e pH to 7.3. The absorbent pad together with the membrane filter is incubated at a suitable temperature, preferably 44° C. in a hot air incubator for a sufficient time, usually between 15 and 60 minutes to allow the uptake of the substrate by the bacteria and its cleavage by the marker enzyme.

The fifth step depends on whether the used substrate was fluorogenic or chemiluminogenic. With a fluorogenic substrate the fifth step comprises irradiating the bacterial microcolonies formed on the membrane filter during the preincubation with light of a wavelength close to the excitation wavelength of the 4-methylumbelliferone, the umbelliferone analog or the fluorescent cleavage product in general, so as to cause the microcolonies to fluoresce. The fluorescent microcolonies can be detected and counted under a UV lamp emitting light of the said wavelength, for example 366 nm, or by using an instrumental technique, e.g. a CCD camera connected to a computer to process the images. When a chemiluminogenic substrate is used the membrane filter is sprayed with an accelerator so as to cause the microcolonies on the filter to become chemiluminescent. This step is preceded by drying the said filter for e.g. 10 min in a hot air incubator at a suitable temperature, for example 60° C. The accelerator may be composed of two components, the first one being a cationic polymer, either or not in combination with a fluorescent dye, e.g. sodium fluorescein and commercially available from Tropix, Inc. as Emerald®, Emerald II®, Sapphire®, Sapphire II®, Nitro-Block® or Ruby®. The second component is an alkalinizing agent such as sodium hydroxide. According to the present invention it was found that the latter can be replaced by a dilute solution, for example 0.5M of an organic base, preferably piperidine, which results in enhanced sensitivity. This new accelerator will further be called "Modified Luminescence Amplifier Material solution" (modified LAM-solution). Alternatively, instead of an accelerator prepared by mixing the two components a commercial mixture can be used such as Galacto-Light® or GUS-Light® (Tropix Inc.). As will be demonstrated hereinafter, it was found surprisingly that on PVDF membrane filters a comparable sensitivity can be obtained by using an accelerator from which the first component has been omitted, that is one consisting of 0.5M piperidine only. This accelerator will further be called "Alternative Accelerator". The luminescent microcolonies can be detected by exposing the membrane filter to X-ray film for e.g. 60 minutes, a high sensitivity Polaroid® film in an ECL camera dedicated to chemiluminescence or by using an instrumental technique, e.g. a CCD camera connected to a computer for image processing.

Further particularities of this invention will become apparent from the following description of six examples. However, this description is not intended to limit the scope of the invention.

DETAILED DESCRIPTION OF THE DRAWINGS

EXAMPLE 1

This example demonstrates the detection and counting of TC and E. coli on a membrane filter in connection with the use of fluorogenic substrates for β-galactosidase or β-glucuronidase, respectively.

Materials:

Membrane filters: 47 mm membrane filters consisting of PVDF (Durapore®, Millipore, Bedford, Mass.), with a pore size of 0.45 μm.

Growth/induction medium: ILM, containing 0.5% maltose, 0.5% tryptone, 0.2% monoammonium phosphate, 0.5% sodium chloride, 0.05% magnesium sulfate, 0.01% sodium dodecyl sulfate, 0.3% yeast extract, 0.01% bile salts, 0.001% cefsulodin, 0.1% dipotassium phosphate and 1% agar (pH 7.3). This medium further either contains 0.001% isopropyl-β-D-thiogalactopyranoside to induce β-galactosidase in TC or 0.05% p-nitrophenyl-β-D-glucuronide to induce β-glucuronidase in E. coli. Buffered assay mixture: 0.1 mol/liter sodium phosphate buffer solution (pH 7.3) containing either 4-trifluoromethylumbelliferyl-β-D-galactopyranoside (TFMU-gal) (substrate for β-galactosidase) or 4-trifluoromethylumbelliferyl-β-D-glucuronide (TFMUG) (substrate for β-glucuronidase) and polymyxin B sulfate (Sigma, 7730 IU/ml). The assay mixture also contains 1 mM magnesium chloride.

Procedure:

100 ml of a water sample containing TC or E. coli was filtered throw,=the membrane filter. The filter was aseptically placed on the growth/induction medium (ILM) and incubated in a water bath at either 37° C. (for TC) or 41.5° C. (for E. coli). After incubation for 6.5 hours, the membrane filters were transferred to a second petri dish containing an absorbent cellulose pad impregnated with 1.8 ml of the buffered assay mixture and incubated for another 30 min at 44° C. Following incubation, the fluorescent microcolonies were counted with the aid of a longwave U; lamp (emitting light at 366 nm)

Figure 1:
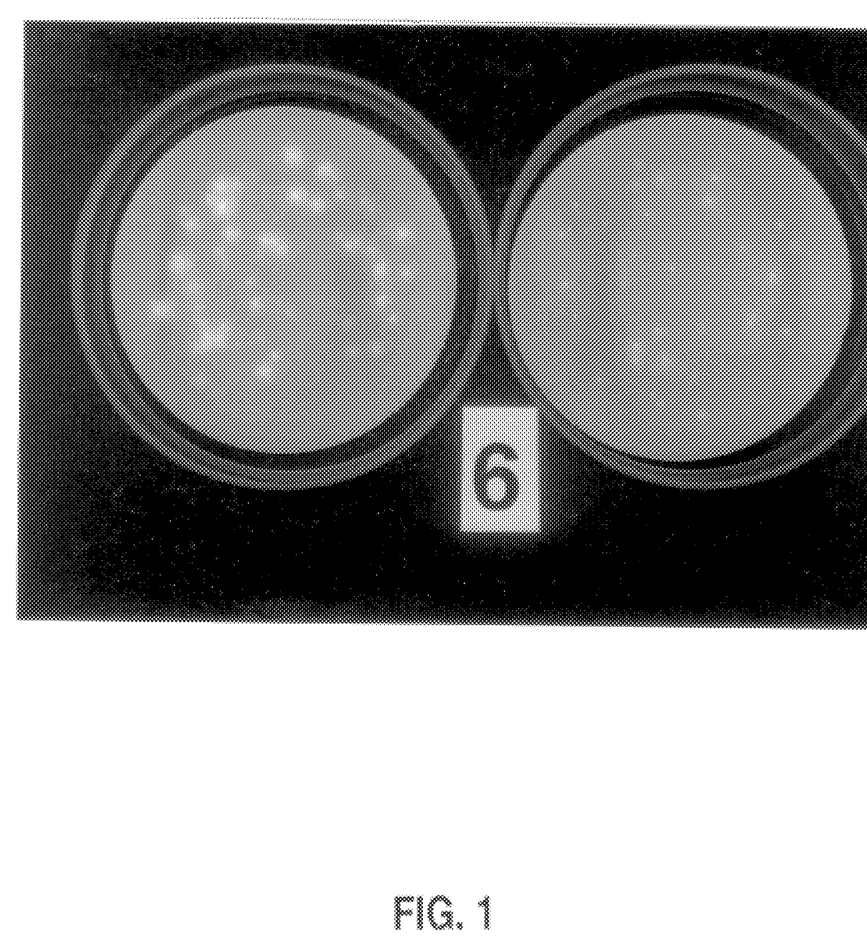
FIG. 1 is a photograph of the appearance of fluorescent microcolonies of TC and E. coli grown on a membrane filter.
Figure 2:
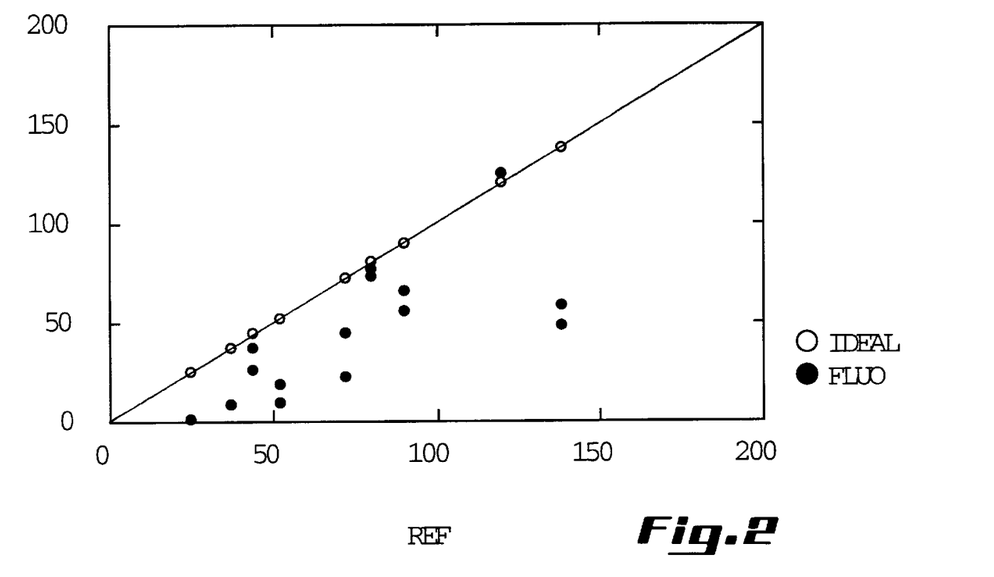
FIG. 2 is a graph correlating counts obtained with the 7-hour fluorescent process for TC on a membrane filter with those obtained on a standard agar medium for the detection of TC.
Figure 3:
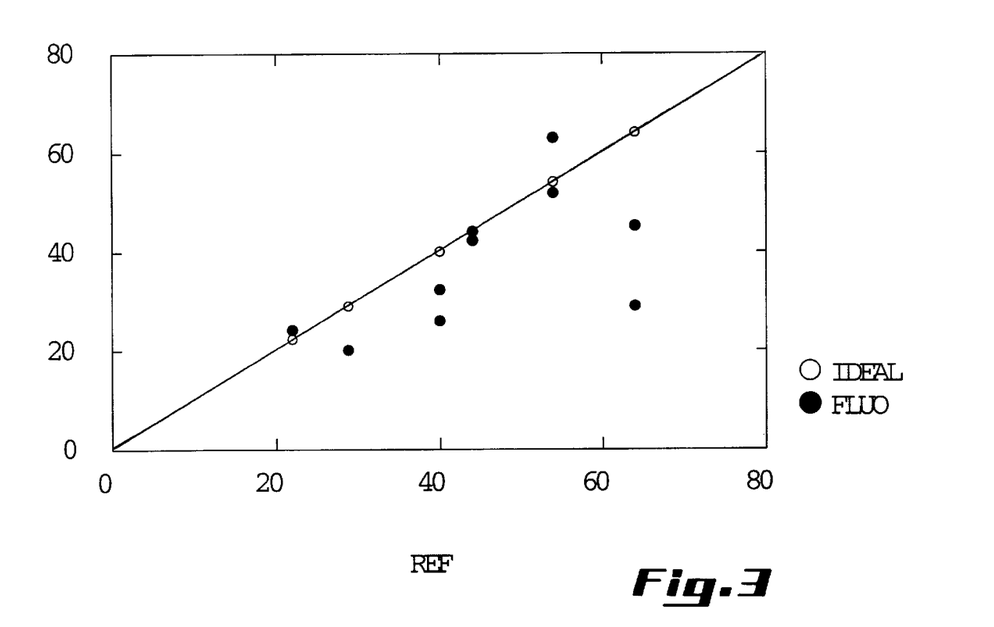
FIG. 3 is a graph correlating counts obtained with the 7-hour fluorescent process for E. coli on a membrane filter with those obtained on a standard agar medium for the detection of E. coli.

Results:

FIG. 1 shows an example of the appearance of the fluorescent microcolonies of TC (left) and E.coli (right) after 6.5 hours of incubation and 30 minutes of enzyme assay. FIG. 2 compares the number of microcolonies of TC counted on the basis of fluorescence with that obtained on a conventional selective agar medium for TC, i.e. m Endo agar LES. FIG. 3 compares the number of microcolonies of E. coli counted on the basis of fluorescence with that obtained by counting on a conventional selective agar medium for E.coli, i.e. m FC agar. The plotted lines represent the ideal correlation curves, and are not fitted to the data. The correlation coefficient between fluorometric counting and counting on a conventional medium was 0.844 for the detection of E. coli and 0.697 for the detection of TC (n=13).

Conclusion:

The method is capable of detecting and enumerating microcolonies of TC and E. coli on the basis of fluorescence within a total time period of 7 hours. The agreement with standard methods was satisfactory.

EXAMPLE 2

This example demonstrates the detection and enumeration of TC and E. coli on a membrane filter in connection with the use of chemiluminogenic substrates for β-galactosidase and β-glucuronidase, respectively.

Materials:

Membrane filters: as described in Example 1. Growth/induction medium: ILM, as described in Example 1.

Buffered assay mixture: 0.1 mol/liter sodium phosphate buffer solution (pH 7.3) containing either Galacton-Plus®, 9 μmol/liter (substrate for β-galactosidase) or Glucuron®, 25 μmol/liter (substrate for β-glucuronidase)(both substrates from Tropix, Inc.) and polymyxin B sulfate (Sigma, 7730 IU/ml). The assay mixture also contains 1 mM magnesium chloride.

Modified Luminescence Amplifier Material-solution (modified LAM-solution): Emerald II® (Tropix Inc.), 1.6 μg/ml in aqueous 0.5 mol/liter piperidine solution.

Procedure:

100 ml of a water sample containing TC or E. coli was filtered through the membrane filter. The filter was aseptically placed on the growth/induction medium (ILM) and incubated in a water bath at either 37° C. (for TC) or 41.5° C. (for E. coli). After incubation for 6 hours, the membrane filters were transferred to a second petri dish containing an absorbent cellulose pad impregnated with 1.8 ml of the buffered assay mixture and incubated for another 30 min at 44° C. Following incubation, the membranes were sprayed with the modified LAM-solution and the chemiluminescent microcolonies were visualised with the aid of X-ray film. To this end the membrane filters were contacted for 1 hour with a Agf a Curix RP1 X-ray film wrapped in polyethylene foil. After development, the luminescent microcolonies appeared as black dots on a transparent background and were counted.

Figure 4:
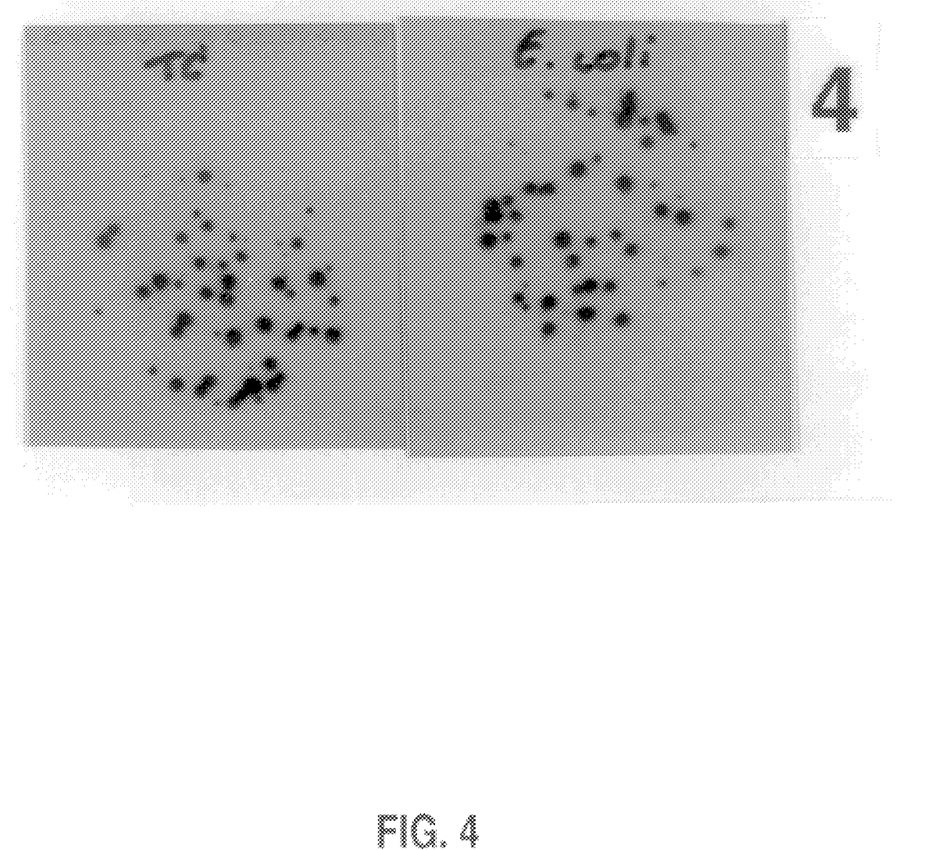
FIG. 4 is a photograph of X-ray film showing chemiluminescent microcolonies of TC and E. coli grown on a membrane filter.
Figure 5:
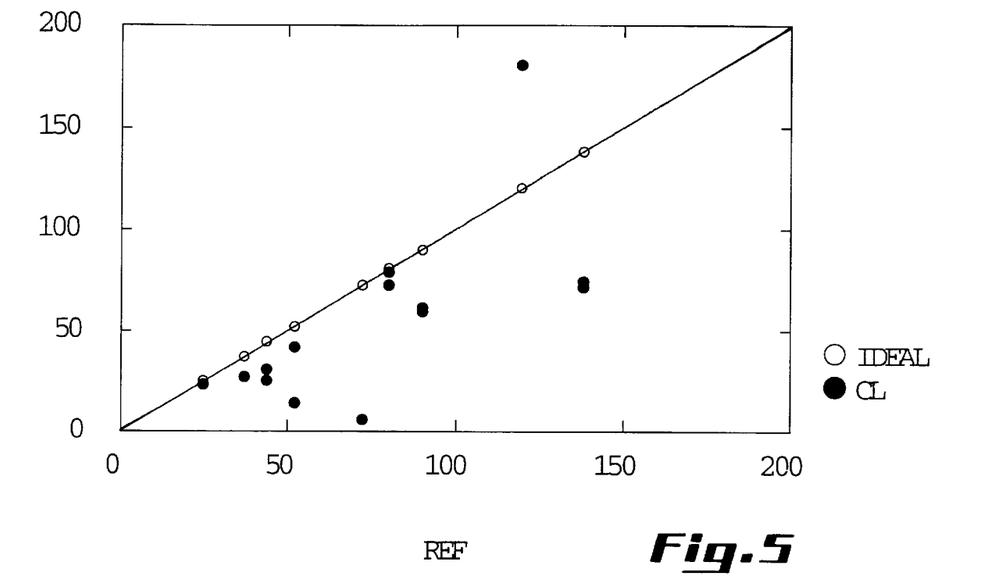
FIG. 5 is a graph correlating counts obtained with the 6.5-hour chemiluminescent process for TC on a membrane filter with those obtained on a standard agar medium for the detection of TC.
Figure 6:
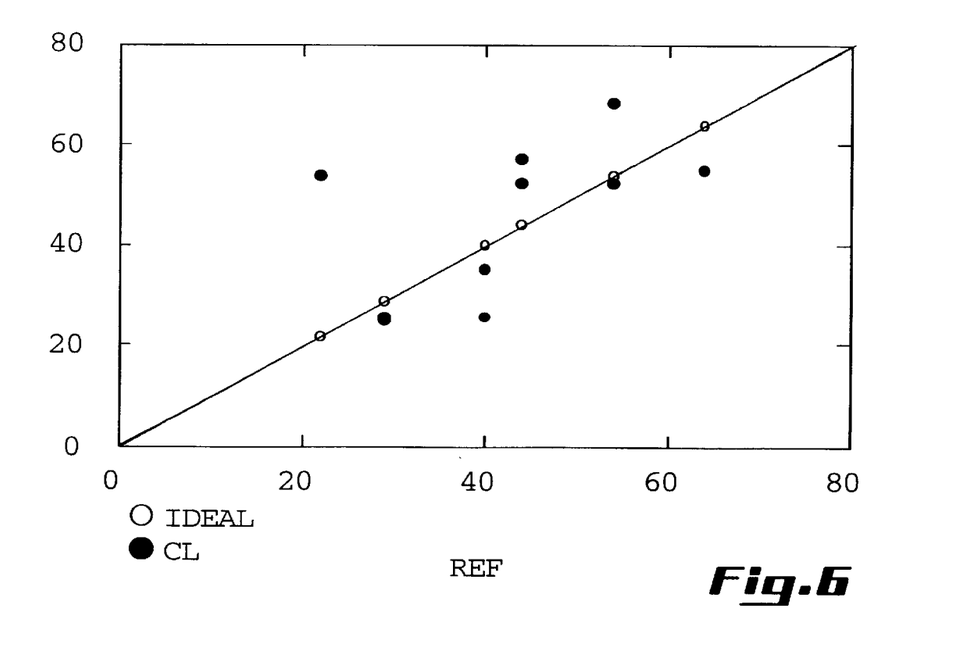
FIG. 6 is a graph correlating counts obtained with the 6.5-hour chemiluminescent process for E. coli on a membrane filter with those obtained on a standard agar medium for the detection of E. coli.

Results:

FIG. 4 shows an example of the appearance of the microcolonies of TC (left) and E. coli (right) on X-ray film after 6 hours of incubation and 30 minutes of enzyme assay. FIG. 5 compares the numbers of microcolonies of TC counted on the basis of chemiluminescence with that obtained by counting conventional selective agar medium for TC, i.e. m Endo agar LES. FIG. 6 compares the numbers of microcolonies of E. coli obtained by counting on the basis of chemiluminescence with that obtained by counting on a conventional selective agar medium for E.coli, i.e. m FC agar. The plotted lines represent the ideal correlation curve, and are not fitted to the data. The correlation coefficient of the chemiluminometric direct counting process compared with conventional media was 0.836 for the detection of E. coli and 0.650 for the detection of TC (n=13).

Conclusion:

The method is capable of detecting and enumerating microcolonies of TC or E. coli on the basis of chemiluminescence within a total time period of 6.5 hours, in particular when an instrumental technique is used, for example with a CCD camera connected to a computer for image processing instead of the X-ray film. The agreement with standard methods was satisfactory.

EXAMPLE 3

This example demonstrates the superiority of polyvinylidenedifluoride (PVDF) filters over conventional filters made of mixed cellulose esters for the enumeration of TC on a membrane filter, based on chemiluminescence.

Materials:

Membrane filters: 47 mm membrane filters consisting of PVDF (Durapore®, Millipore, Bedford, Mass.), with a pore size of 0.45 µm.

47 mm membrane filters made of mixed cellulose esters, with a pore size of 0.45 µm (Millipore).

Growth/induction medium: ILM, containing 0.5% maltose, 0.5% tryptone, 0.2% monoammonium phosphate, 0.5% sodium chloride, 0.05% magnesium sulfate, 0.01% sodium dodecyl sulfate, 0.3% yeast extract, 0.01% bile salts, 0.001% cefsulodin, 0.1% dipotassium phosphate and 1% agar (pH 7.3). This medium further contains 0.001% isopropyl-β-D-thiogalactopyranoside to induce β-galactosidase in TC.

Buffered assay mixture: 0.1 mol/liter sodium phosphate buffer solution (pH 7.3) containing Galacton-Plus® (Tropix, Inc.), 9 µmol/liter and polymyxin B sulfate (Sigma, 7730 IU/ml). The assay mixture also contains 1 mM magnesium chloride.

Modified Luminescence Amplifier Material-solution (modified LM-solution): as described in Example 2.

Procedure:

100 ml of a water sample containing TC was filtered through the membrane filter. The filter was aseptically placed on the growth/induction medium (ILM) and incubated in a water bath at 37° C. After incubation for 6 hours, the membrane filter was transferred to a second petri dish containing an absorbent cellulose pad impregnated with 1.8 ml of the buffered assay mixture and incubated for another 30 min at 44° C. Following incubation, the membrane was sprayed with the modified LAM-solution and the chemiluminescent microcolonies were then visualised with the aid of X-ray film, as described in Example 2.

Figure 7:
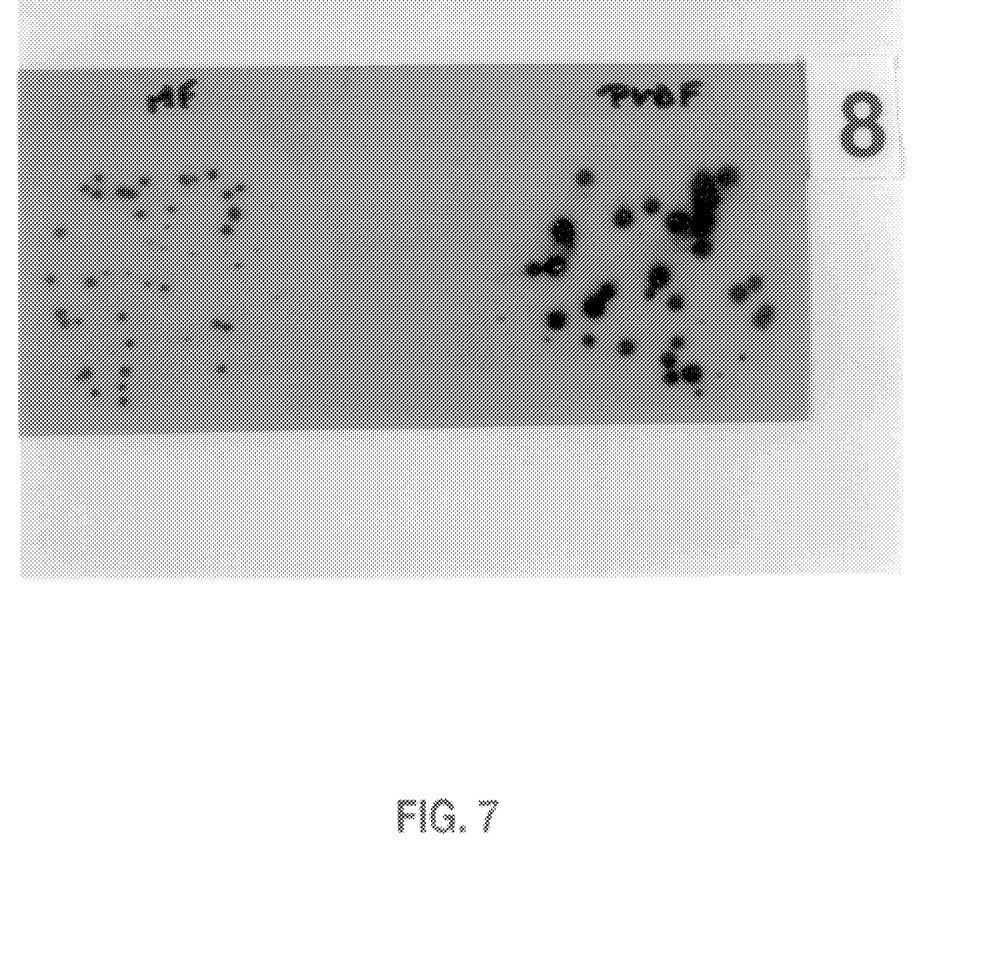
FIG. 7 is a photograph of X-ray film showing the increased intensity of the microcolonies of TC on polyvinylidenedifluoride (PVDF) membrane filters compared to the intensity on membrane filters made of mixed cellulose esters.

Results:

FIG. 7 is a picture showing the increased intensity of the microcolonies of TC on PVDF membrane filters relative to the intensity obtained on membrane filters made of mixed cellulose esters.

Conclusion:

Membrane filters made of PVDF yield more intensely chemiluminescent microcolonies of coliforms than filters made of mixed cellulose esters, thus improving the detectability of the bacteria.

EXAMPLE 4

This example demonstrates that the visualisation of total coliforms on a membrane filter based on chemiluminescence can be performed with a dilute solution of an organic base without the addition of a cationic polymer and a fluorescent dye when hydrophobic membrane filters, in particular PVDF (Durapore®) are used to concentrate the bacteria present in the sample.

Materials:

Membrane filters: as described in example 1. Growth/induction medium ILM, as described in Example 3.

Buffered assay mixture: as described in Example 3. Modified Luminescence Amplifier Material-solution (modified LAM-solution): as described in Example 2. Accelerator without cationic polymer and fluorescent dye: aqueous 0.5M piperidine (called "Alternative Accelerator")

Procedure:

As described in Example 3, except that following incubation, the membrane was sprayed either with the modified LAM-solution or the Alternative Accelerator. The chemiluminescent microcolonies were then counted with the aid of X-ray film, as described in Example 2.

Figure 8:
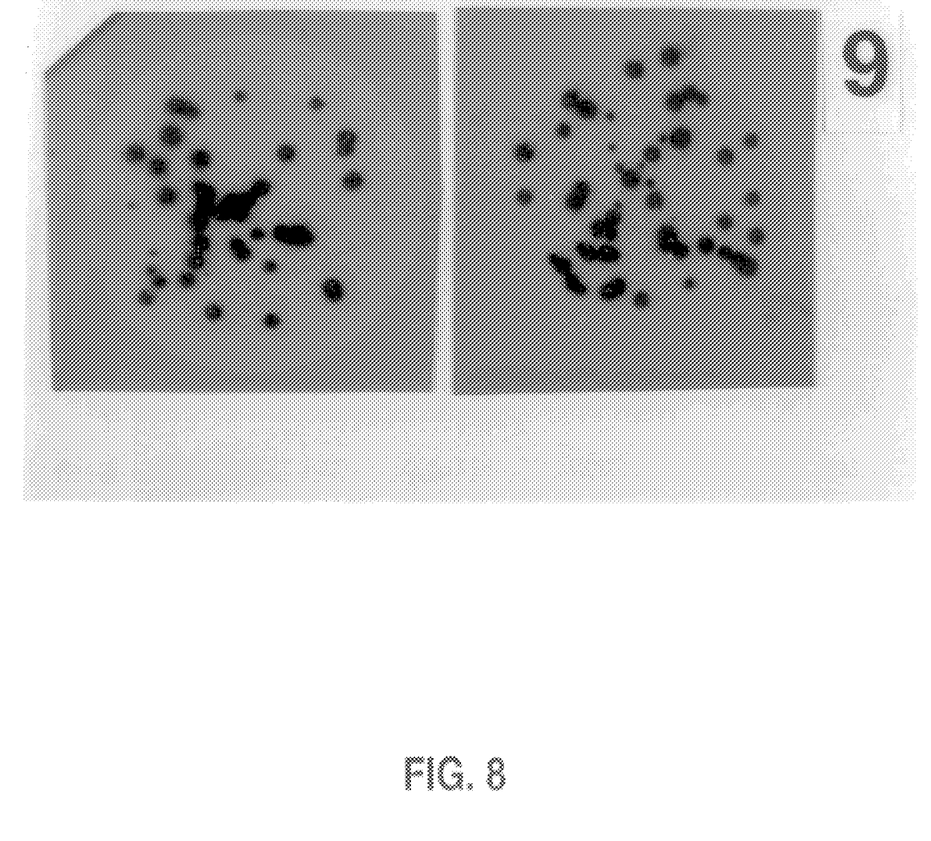
FIG. 8 is a photograph of X-ray film showing the comparable sensitivity obtained for TC when said PVDF filter is sprayed with an accelerator that contains only piperidine (Alternative Accelerator), with reference to spraying with a modified LAM-solution.

Results:

FIG. 8 illustrates the comparable sensitivity obtained by spraying a PVDF filter with an accelerator that contains only piperidine (Alternative Accelerator, right), with reference to spraying with an accelerator containing piperidine and a Luminescence Amplifying Material (left).

Conclusion:

The hydrophobic environment, created by the PVDF filter protects the enzymatic cleavage product, which makes the use of a protective cationic polymer superfluous and, hence, allows the use of an accelerator that consists of only piperidine.

EXAMPLE 5

This example demonstrates the superiority of the ILM over conventional selective media for the detection of TC and/or E. coli, in connection with the enumeration of E. coli on a membrane filter, based on the chemiluminometric detection of either β-galactosidase or β-glucuronidase.

Materials:

Membrane filters: as described in Example 1. Bacterial strain: E. coli, No. 2, isolated from a natural well water. An appropriate dilution of an overnight culture in tryptic soy broth w/o dextrose (DIFCO) was added to sterile distilled water, so as to obtain a concentration of approximately 100 CFU/100 ml. Growth/induction media: ILM, containing 0.5% maltose, 0.5% a tryptone, 0.2% monoammonium phosphate, 0.5% sodium chloride, 0.05% magnesium sulfate, 0.01% sodium dodecyl sulfate, 0.3% yeast extract, 0.01% bile salts, 0.001% cefsulodin, 0.1% dipotassium phosphate and 1% agar (pH 7.3). This medium either contains 0.01% isopropyl-β-D-thiogalactopyranoside to induce β-galactosidase or 0.005% p-nitrophenyl-β-D-glucuronide to induce β-glucuronidase.

- Lauryl Tryptose agar: Lauryl Tryptose broth (Difco, Detroit, Mich.) to which 1% agar was added, as such (β-galactosidase) or supplemented with 0.005% p-nitrophenyl-β-D-glucuronide (β-glucuronidase).
- EC agar: EC-broth (Difco) to which 1% agar was added, as such (β-galactosidase) or supplemented with 0.005% p-nitrophenyl-β-D-glucuronide (β-glucuronidase).
- m T7 agar (Difco), as such (β-galactosidase) or supplemented with 0.005% p-nitrophenyl-β-D-glucuronide (β-glucuronidase)
- m TEC agar (Difco), as such (β-galactosidase) or supplemented with 0.005% p-nitrophenyl-β-D-glucuronide (β-glucuronidase).
- m FC agar (Difco), as such (β-galactosidase) or supplemented with 0.005% p-nitrophenyl-β-D-glucuronide (β-glucuronidase).
- MacConkey agar (Difco), as such (β-galactosidase) or supplemented with 0.005% p-nitrophenyl-β-D-glucuronide (β-glucuronidase).
- m Endo agar LES (Difco), as such (β-galactosidase) or supplemented with 0.005% p-nitrophenyl-β-D-glucuronide (β-glucuronidase).
- Lauryl Sulphate agar: Lauryl Sulphate broth (Oxoid, Ltd., Basingstoke, U.K.) to which 1% agar was added, as such (β-galactosidase) or supplemented with 0.005% p-nitrophenyl-β-D-glucuronide (β-glucuronidase).
- Tryptone Bile agar: containing 2% tryptone, 0.16% bile salts and 1% agar, to which further 0.01% isopropyl-β-D-thiogalactopyranoside (β-galactosidase) or 0.005% p-nitrophenyl-β-D-glucuronide (β-glucuronidase) was added,
- MUG-7 agar: medium as described by Sarhan and Foster (cited above), but with MUG omitted and 0.01% isopropyl-β-D-thiogalactopyranoside (β-galactosidase) or 0.005% p-nitrophenyl-β-D-glucuronide (β-glucuronidase) added,
- medium disclosed in the Berg et al. U.S. patent (cited above), but with MU-gal omitted, as such (β-galactosidase) or supplemented with 0.005%p-nitrophenyl-β-D-glucuronide (β-glucuronidase). Buffered assay mixture: as described in Example 2. Modified Luminescence Amplifier Material-solution (modified LAM-solution): Sapphire II (Tropix, Inc.) 1.6 µg/ml in aqueous 0.5 mol/liter piperidine solution.

Procedure:

As described in Example 2. Except that in addition to the ILM a variety of other growth/induction media were used.

Figure 9:
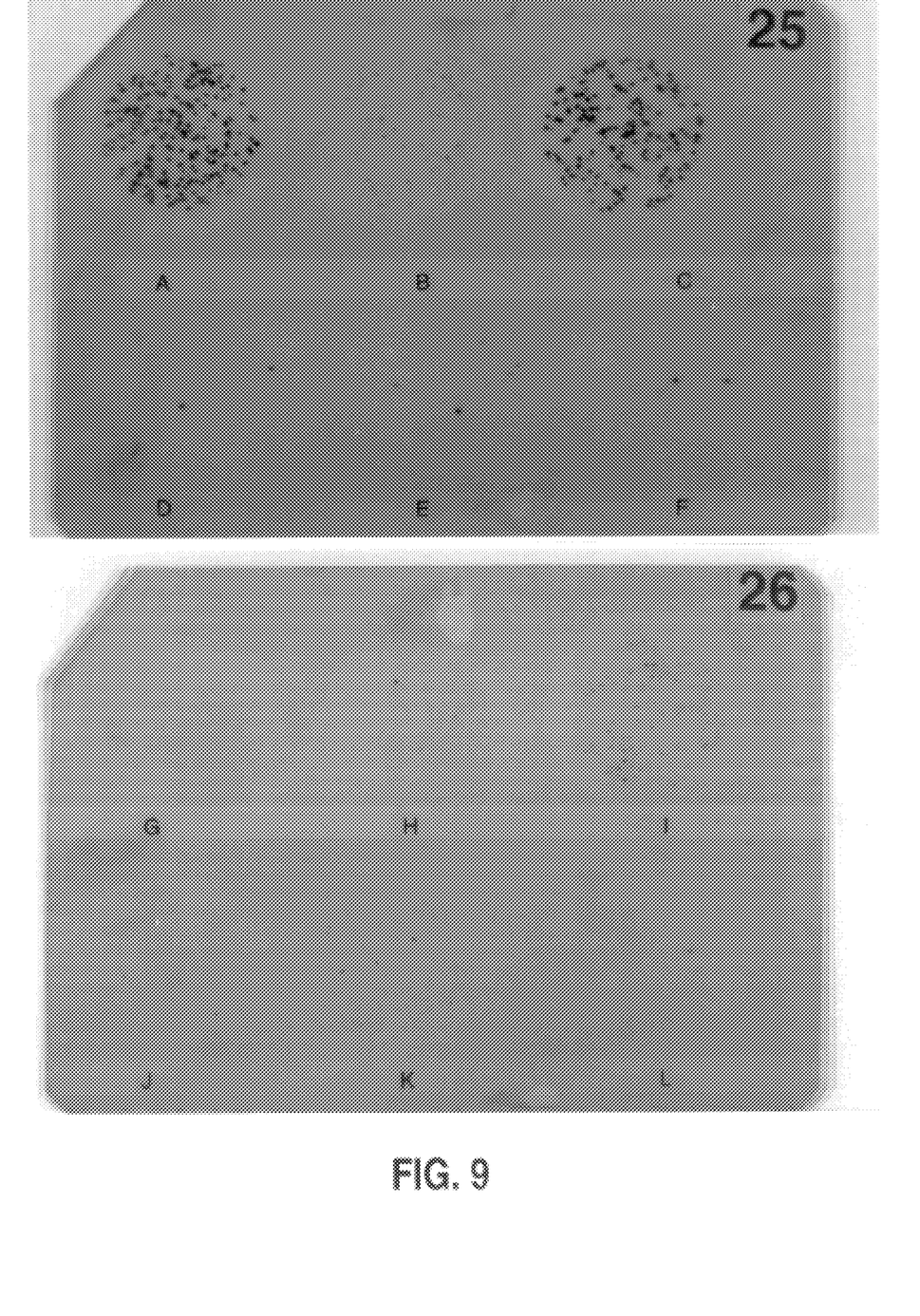
FIG. 9 is a picture showing the superiority of the ILM relative to other (commercial) selective media for the detection of TC and/or E. coli, in connection with the enumeration of E. coli on a membrane filter based on chemiluminometric measurement of β-galactosidase activity.

Results:

FIG. 9 is a picture showing the superiority of the ILM (A) relative to other.(commercial) selective media (B to L) for the detection of TC and/or E. coli, in connection with the enumeration of E. coli on a membrane filter based on chemiluminometric measurement of β-galactosidase activity, wherein B=the MUG-7 medium as described by Sarhan and Foster (cited above), C=Tryptone Bile agar, D=the medium disclosed in the Berg et al. U.S. patent (cited above), E=Lauryl Tryptose agar, F=EC agar, G=m T7 agar, H=m TEC agar, I=MacConkey agar, J=m FC agar, K=m Endo agar LES and L=Lauryl Sulphate agar.

Figure 10:
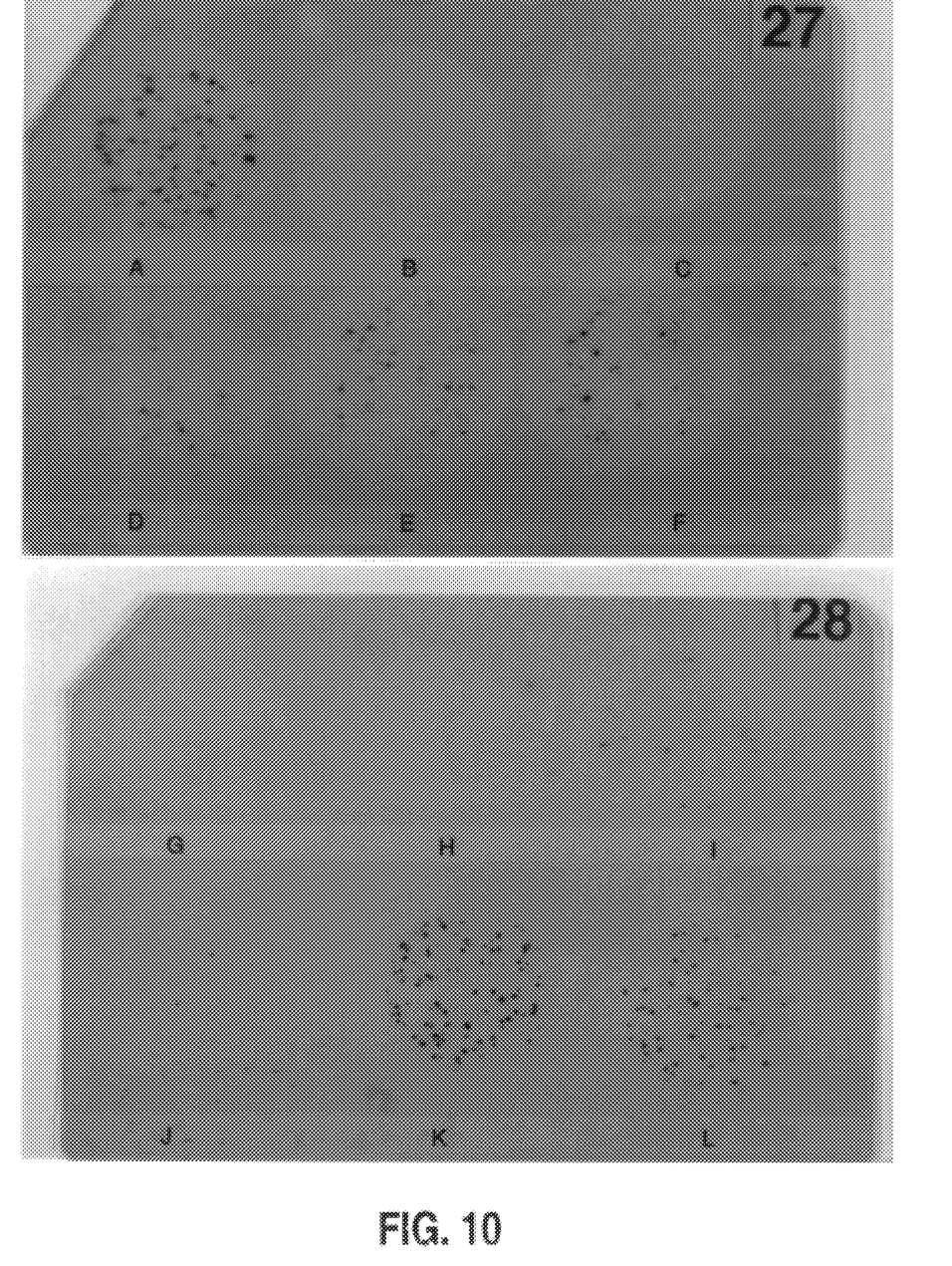
FIG. 10 is a picture showing the superiority of the ILM relative to other selective media for the detection of TC and/or E. coli, in connection with the enumeration of E. coli on a membrane filter based on chemiluminometric measurement of β-glucuronidase activity.

FIG. 10 is a picture showing the superiority of the ILM (A) relative to other (commercial) selective media (B to L) for the detection of TC and/or E. coli, in connection with the enumeration of E. coli on a membrane filter based on chemiluminometric measurement of β-glucuronidase activity, wherein B=the MUG-7 medium as described by Sarhan and Foster (cited above), C=Tryptone Bile agar, D=the medium disclosed in the Berg et al. U.S. patent (cited above), E=Lauryl Tryptose agar, F=EC agar, G=m T7 agar, H=m TEC agar, I=MacConkey agar, J=m FC agar, K=m Endo agar LES and L=Lauryl Sulphate agar, all media supplemented with 0.005% p-nitrophenyl-β-D-glucuronide.

Conclusion:

The use of the ILM is an important feature for the optimal performance of the method according to this invention for the detection of microcolonies on the basis of β-galactosidase or of β-glucuronidase activity.

EXAMPLE 6

Materials:

Bacterial strain: as described in Example 5. Membrane filters as described in Example 1. Growth/induction medium with yeast extract: ILM, as described in Example 1, containing 0.05% p-nitrophenyl-β-D-glucuronide to induce β-glucuronidase.

Growth/induction medium without yeast extract: the ILM, as described in Example 1 but with omission of the yeast extract and containing 0.05% p-nitrophenyl-β-D-glucuronide to induce β-glucuronidase.

Buffered assay mixture: 0.1 mol/liter sodium phosphate buffer solution (pH 7.3) containing Glucuron® (Tropix, Inc.), 25 µmol/liter and polymyxin B sulfate (Sigma, 7730 IU/ml). The assay mixture also contains 1 mM magnesium chloride.

Modified Luminescence Amplified Material solution (modified LAM solution): as described in Example 5.

Procedure:

E. coli was detected and counted on a membrane filter based on chemiluminescence, as described in Example 2, using Glucuron as a substrate but with omission of the yeast extract from the Improved Luminescence Medium (ILM).

Figure 11:
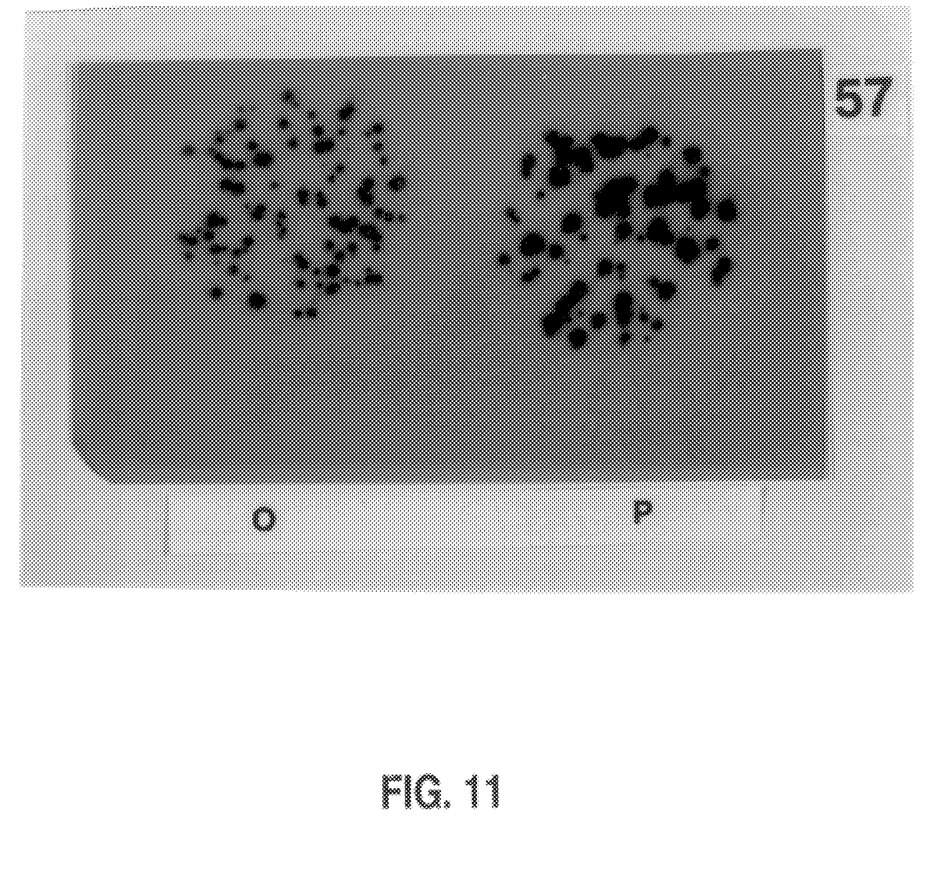
FIG. 11 is a picture showing the improved chemiluminescent response obtained by using the ILM without yeast extract, relative to the complete ILM, for preincubation.

Result:

FIG. 11 illustrates the enhanced chemiluminescent response for E. coli obtained by using the ILM without yeast extract (right), relative to the complete ILM (left), for preincubation.

Conclusion:

The ILM without yeast extract improves the intensity of the luminescent colonies on a membrane filter, in comparison to the complete ILM with yeast extract.

I claim:

1. An enzymatic method for detecting coliform bacteria, in a liquid or liquefied sample comprising the steps of:
    a) concentrating the bacteria on a membrane filter;
    b) placing the membrane filter and the bacteria concentrated thereon on a growth medium containing nutrients to support propagation of the bacteria and an inducer for inducing a marker enzyme in the course of their growth and metabolism;
    c) preincubating the membrane filter and the bacteria concentrated thereon to form microcolonies of these bacteria on the membrane filter and to produce said marker enzyme; and d) making the microcolonies visible by means of luminescence, characterized in that said microcolonies are made visible by an enzyme assay comprising:

removing the membrane filter from the growth medium after said preincubation step (c);

treating the microcolonies on the membrane filter with a membrane permeabilizer and contacting them with a chemiluminogenic or fluorogenic substrate for said marker enzyme;

incubating the microcolonies to allow cleavage of said substrate so as to produce a chemiluminescent or fluorescent product; and triggering light emission from the chemiluminescent or fluorescent product produced by the microcolonies.

2. The method according to claim 1, characterized in that after said preincubation step (c), the membrane filter is placed on an assay medium containing said membrane permeabilizer and said substrate.

3. The method according to claim 1, wherein the membrane filter is more hydrophobic than cellulose ester filters.

4. A method according to claim 1, wherein the inducer is an inducer of β-galactosidase and the fluorogenic substrate comprises a fluorogenic galacto-pyranoside.

5. A method according to claim 1, wherein the inducer is an inducer of β-glucuronidase and the fluorogenic substrate comprises a fluorogenic glucuronide.

6. A method according to claim 1, wherein the inducer is an inducer of β-galactosidase and the chemiluminogenic substrate comprises a chemiluminogenic galactopyranoside.

7. A method according to claim 1, wherein the inducer is an inducer of β-glucuronidase and the chemiluminogenic substrate comprises a chemiluminogenic glucuronide.

8. The method according to claim 8, characterized in that the chemiluminescent product produced by cleavage of the chemiluminogenic substrate is chemically triggered by an accelerator solution containing a dilute solution of an organic base.

9. The method according to claim 10, wherein the membrane filter is more hydrophobic than cellulose ester filters.

10. The method according to claim 1, wherein the membrane perineabilizer comprises polymyxin B and/or colistin methanesulfonate.

11. The method according to claim 1, wherein said growth medium comprises mineral nutrients, a protein hydrolysate, and a sugar or a polyalcohol.

12. The growth medium for use in a method according to claim 1, comprising mineral nutrients, a protein hydrolysate, an inducer for inducing a marker enzyme in the course of growth and metabolism of coliform bacteria, and a sugar or a polyalcohol.

13. The growth medium according to claim 12, characterized in that said mineral nutrients comprise monoammonium phosphate, dipotassium hydrogen phosphate, sodium chloride and magnesium sulfate.

14. The growth medium according to claim 12, comprising inhibitors of non-coliform bacteria.

15. A method according to claim 1, characterized in that said inducer is an inducer of β-galactosidase and detects faecal or total coliform bacteria.

16. A method according to claim 1, characterized in that said inducer is an inducer of β-glucuronidase and detects *E. coli*.

17. A method according to claim 7, wherein the chemiluminescent product produced by cleavage of the chemiluminogenic substrate is chemically triggered by an accelerator solution containing a dilute solution of an organic base.

18. The method according to claim 17, wherein the membrane filter is more hydrophobic than cellulose ester filters and said accelerator solution consists mainly of a dilute solution of said organic base only.

19. A method according to claim 15, wherein the β-galactosidase inducer is a compound selected from the group consisting of isopropyl-β-D-thiogalactopyranoside and meliboise.

20. A method according to claim 16, wherein the β-glucuronidase inducer is a compound selected from the group consisting of isopropyl-β-D-thio-glucuronide, pnitrophenyl-β-D-glucuronide, p-nitrophenyl-β-D-glucuronide and o-nitro-phenyl-β-D-glucuronide and methyl-β-D-glucuronide.

21. The method according to claim 3, wherein the membrane filter comprises polyvinylidenedifluoride (PVDF).

22. The method according claim 4, wherein the fluorogenic galacto-pyranoside is a umbelliferyl-β-D-galactopyranoside.

23. The method according to claim 22, wherein the umbelliferyl-β-D-galactopyranoside is 4-trifluoromethyl-umbelliferyl-β-D-galactopyranoside (TFMU-gal).

24. The method according to claim 5, wherein the fluorogenic glucuronide is an umbelliferyl-β-D-glucuronide.

25. The method according to claim 24, wherein the umbelliferyl-β-D-glucuronide is 4ethyl-umbelliferyl-β-D-glucuronide (TFMUG).

26. The method according to claim 6, wherein the chemiluminogenic galactopyranoside is 3-(4-methoxyspiro(1,2-dioxetane-3,2'-tri-cyclo (3.3.1.1$^{3,7}$)decan)-4-yl)phenyl-β-D-galactopyranoside (AMPGD) or a derivative thereof.

27. The method according to claim 26, wherein the derivative of 4-methoxyspiro(1,2-dioxetane-3,2'-tri-cyclo (3.3.1.1$^{3,7}$)decan)-4-yl)phenyl-β-D-galactopyranoside is a chloro derivative.

28. The method according to claim 7, wherein the chemiluminogenic glucuronide is (3-(4methoxyspiro-(1,2-dioxetane-3,2'-(5'-chloro)-tricyclo(3.3.1.1$^{3,7}$)decan)-4-yl) phenyl)-β-D-glucuronide or a derivative thereof.

29. The method according to claim 8, wherein the organic base comprises piperidine.

30. The method according to claim 9, wherein the membrane filter comprises polyvinylidene-difluoride (PVDF) and said accelerator solution consists mainly of a dilute solution of said organic base.

31. The method according to claim 30, wherein the organic base comprises piperidine.

32. The method according to claim 11, wherein said growth medium comprises mineral nutrients, the protein hydrolysate tryptone, and either the sugar maltose or the polyalcohol mannitol.

33. A growth medium according to claim 12, comprising mineral nutrients, the protein hydrolysate tryptone, either an inducer of β-galactosidase or an inducer of β-glucuronidase, and either the sugar maltose or the polyalcohol mannitol.

34. A growth medium according to claim 14, wherein said inhibitors of non-coliform bacteria are selected from the group consisting of sodium dodecyl sulfate, bile salts and ccfsulodin.

35. A method according to claim 17, wherein the organic base comprises piperidine.

36. A method according to claim 18, wherein the membrane filter comprises polyvinylidenedifluoride (PVDF) and said organic base comprises piperidine.

* * * * *